(12) United States Patent
Davey

(10) Patent No.: US 8,697,146 B2
(45) Date of Patent: Apr. 15, 2014

(54) POLY-HAPTEN WITH TOPICAL HORMONE ALOPECIA HAIR REGROWTH SYSTEM

(75) Inventor: George Davey, West Des Moines, IA (US)

(73) Assignee: A66 Incorporated, Wilmington, DE (US)

( * ) Notice: Subject to any disclaimer, the term of this patent is extended or adjusted under 35 U.S.C. 154(b) by 3 days.

(21) Appl. No.: 13/305,280

(22) Filed: Nov. 28, 2011

(65) Prior Publication Data

US 2013/0136700 A1    May 30, 2013

(51) Int. Cl.
*A01N 65/00* (2009.01)
*A01N 25/00* (2006.01)

(52) U.S. Cl.
USPC .......................................... 424/725; 514/880

(58) Field of Classification Search
None
See application file for complete search history.

(56) References Cited

U.S. PATENT DOCUMENTS

| 2005/0208853 A1* | 9/2005 | Hendrix et al. ................. 442/97 |
| 2006/0029455 A1* | 2/2006 | Baines et al. .................... 401/21 |
| 2006/0211766 A1* | 9/2006 | Kaplan et al. ................. 514/529 |

FOREIGN PATENT DOCUMENTS

| EP | 327263 A1 * | 8/1989 |
| WO | WO 9625943 A1 * | 8/1996 |
| WO | WO 2009158687 A1 * | 12/2009 |

OTHER PUBLICATIONS

Monk, "Induction of Hair Growth in Alopecia Totalis with Diphencyprone Sensitization," Clinical and Experimental Dermatology, vol. 14, Issue 2, pp. 154-157 (1989).*
Buckley et al, "The Therapeutic Use of Topical Contact Sensitizers in Benign Dermatoses," British Journal of Dermatology, vol. 145, No. 3, pp. 385-405 (2001).*

* cited by examiner

*Primary Examiner* — Patricia A Duffy
*Assistant Examiner* — Dennis J Parad

(57) ABSTRACT

A hair regrowth system consisting of sensitization, growth, and maintenance kits for alopecia areata and related alopecia balding conditions. Graduated doses of specific engineered and or extracted haptens are included in a sensitization kit for initiating immune system response in hairless areas. A growth kit containing topical hormones to increase papilla size and vigor and a maintenance kit to sustain immune system response and papilla size and vigor for the long term are included in some embodiments.

8 Claims, 2 Drawing Sheets

POLY-HAPTEN WITH TOPICAL HORMONE ALOPECIA HAIR REGROWTH SYSTEM

FIELD OF THE INVENTION

The present invention relates generally to means and method of reversing alopecia areata, or treating other hair loss conditions, at least temporarily and, specifically to a kit and substance employed to trigger an immune response through contact dermatitis using Urushiol.

BACKGROUND

Alopecia areata is an autoimmune disease associated with hair follicles that can result in hair loss. Hair loss resulting from alopecia areata can occur anywhere on the body and can be patchy hair loss or total hair loss. Other similar conditions that can result in hair loss include, for example, pattern baldness, hypotrichosis, and other types of alopecia including, for example, alopecia androgenetica, alopecia areata diffusa, alopecia areata ophiasis, alopecia barbae, alopecia cicatricial, alopecia marginalis, alopecia mucinosa, alopecia partialis, alopecia totalis, alopecia universalis, congenial alopecia, reticular alopecia areata, sisaipho alopecia areata, syphilitic alopecia, and traction alopecia.

Dermatologists typically treat alopecia and related balding conditions with chemical agents such as cortical steroids and squaric acid dibutyl ester (SADBE). SADBE causes an immune system response known as contact dermatitis, which sensitizes the immune system, thereby assisting the immune system in decreasing underlying inflammation responsible for the hair loss. Cortical steroids suppress all immune system response. However, this type of treatment is only successful for a percentage of the population because different people have different sensitivity thresholds and, in fact, many people have no reaction to the SADBE agents at all rendering it completely ineffective in those cases. Cortical steroids likewise only work in a percentage of the population. Exactly how this or other contact sensitizers work is not really known. It is thought that it could be antigen competition, that they divert the attention of the inflammatory cells to them, thus moving them away from the hair follicles and allowing the affected area to re-grow.

Other means of treating hair loss have been disclosed. Some of these are disclosed in United States patents or applications. For example, U.S. patent application Ser. No. 11/471,827 discloses a composition that includes dihydrotestosterone blocker and a thyroid source. Alternatively, the composition may include an estrogen source and a thyroid source relates to uses of T3 (triiodothyronine) but does not disclose an immune sensitizer or any contact dermatitis agent. U.S. patent application Ser. No. 10/077,289 describes compositions which allegedly stimulate stem cells and/or bulge cells to create new hair follicular cells, to enhance blood flow to hair follicles resulting in the activation and transition of stem cells to active cells yielding terminal hair growth. The active molecule reported in this invention are naturally occurring phytosterol, particularly, 13-sitosterol. In general, for topical administration, formulated in combination with one or more excipients. U.S. patent application Ser. No. 10/584,766 relates to the use of IL-15 polynucleotides, polypeptides or compounds which bind to an antibody which specifically recognizes the IL-15 polypeptide or which specifically bind to an IL-15 receptor alpha chain for the preparation of a composition described as stimulating hair growth or for treating, preventing and/or ameliorating hair loss. U.S. patent application Ser. No. 11/089,146 purports to provides methods and compositions for treating hair loss, including arresting and/or reversing hair loss and/or promoting hair growth, in mammals, such as humans, companion animals and livestock, using certain thyromimetic compounds. U.S. patent application Ser. No. 12/996,899 discloses a composition comprising cardiac glycoside which may be the only active ingredient present in the composition. The cardiac glycoside may be adjunctively administered with at least one active ingredient, i.e. the composition may further comprise adjuvant compounds which exhibit efficacy in treating hair loss disorders and may comprise at least one component selected from the group consisting of a steroid, an indole-based compound, an anti-fungal agent, an anti-inflammatory agent and a cooling or antipruritic agent.

SUMMARY

This summary is provided to introduce a selection of concepts in a simplified form that are further described below in the Detailed Description. This summary is not intended to identify key features or essential features of the claimed subject matter, nor is it intended to be used, in isolation, as an aid in determining the scope of the claimed subject matter. At a high level, embodiments of the invention relate to a hair re-growth method dependent upon self-inflicted contact dermatitis and followed by follicle hormone stimulation to induce hair regrowth and a kit or method that includes Urushiol.

Various embodiments of the hair re-growth method can be used for treating and/or preventing, hair loss. "Hair loss," as the term is used herein refers to a loss of hair that can result from any number of conditions, diseases, or the like, including, for example, alopecia and hypotrichosis.

Urushiol is present in the oil produced by the poison ivy plant and several other plants. It may also be engineered. Many people have a high sensitivity to Urushiol, estimates are that 85% of the population will show allergic reaction to it. By utilizing embodiments of the invention, a larger percentage of the population in need of treatment for hair loss can be successfully treated by using Urushiol to enhance an immune system response in those for whom SADBE alone is ineffective. In some embodiments, for example, the treatment success can be expanded to approximately 95% of the population in need of treatment.

A Hapten is a type of antigen that elicits production of antibodies only when combined with another antigenic molecule, such as immunogen. It can also react with previously existing antibodies. An example of a hapten is Urushiol but there are many. The method of the present invention also contemplates using mixtures of haptens where the mixture includes Urushiol.

A first illustrative embodiment of the present invention relates to simply applying a Urushiol mixture to the affected area i.e. the area where hair loss is evident until the area becomes sensitized (a reaction can be detected). On occasion this simple stimulation of the immune system may induce hair regrowth.

A second illustrative embodiment of the present invention relates to a method of reversing hair loss that includes application of specific and multiple doses at a level determined to be at or near the sensitization threshold of the user over a specific time period of a preparation that includes Urushiol.

A third illustrative embodiment of the present invention relates to a method of reversing hair loss that starts with a first phase. A preparation made with at least Urushiol is applied to the area where hair loss has occurred over a given time period to determine an appropriate level that causes adequate sensitization of the affected area. The method may include recommendations for how much, how often and how many times the preparation should be used to determine sensitization level. The sensitization dosage of Urushiol in the preparation may be the same and used a plurality of time throughout the time period of a second phase or may be of graduated dosage of one or more ingredients, including Urushiol, or may vary in accordance with the method. A third phase may then be employed where level of the preparation containing Urushiol is applied less often with the objective of maintaining hair regrowth. If hair regrowth ceases or slows, the user may begin the first phase again and proceed until results are achiever.

Another embodiment may employ the same approach as the third embodiment just described and further includes application to the area of hair loss of a preparation made with at least one, and perhaps a combination of several, thyroid and other hormone(s) including prostaglandins and prostaglandin analogs to stimulate the follicles to a state where hair regrowth occurs. This preparation may also be used to first determine a sensitization dose, then applied in a routine purposed to start regrowth and, thereafter, with less frequent applications for maintenance. The method may include recommendations for how much, how often and how many times the hormone preparation should be used. Further, the dosage and relative levels of hormone(s) may be of uniform dosage or may include graduated dosages of some or all of the hormone(s) in the preparation for use in determining sensitization dosage to use during the second phase, regrowth. Finally, the embodiment may include a third preparation. This one is intended to maintain the hair follicles in a state stimulated to continue normal hair growth. While this routine may be all that is necessary for a given patch of baldness, it may be repeated as needed. Further, the method may include more or less applications of the Urushiol preparation as compared to the preparation including hormones. Finally, the method may include an alternation of the Urushiol preparation and the hormone preparation, or may recommend an alternating pattern of application of these two preparations or recommend some other pattern prior to recommending application of the maintenance preparation. It is intended there will be kits with and without hormones as needed to treat the affected population.

These and other aspects of the invention will become apparent to one of ordinary skill in the art upon a reading of the following description, drawings, and the claims.

BRIEF DESCRIPTION OF THE DRAWINGS

The present invention is described in detail below with reference to the attached drawing figures, wherein.

DETAILED DESCRIPTION

The subject matter of embodiments of the invention disclosed herein is described with specificity to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other technologies. Moreover, although the term "step" is used herein to connote different elements of methods employed, the term should not be interpreted as implying any particular order among or between various steps herein disclosed unless and except when the order of individual steps is explicitly described.

Figure 1:
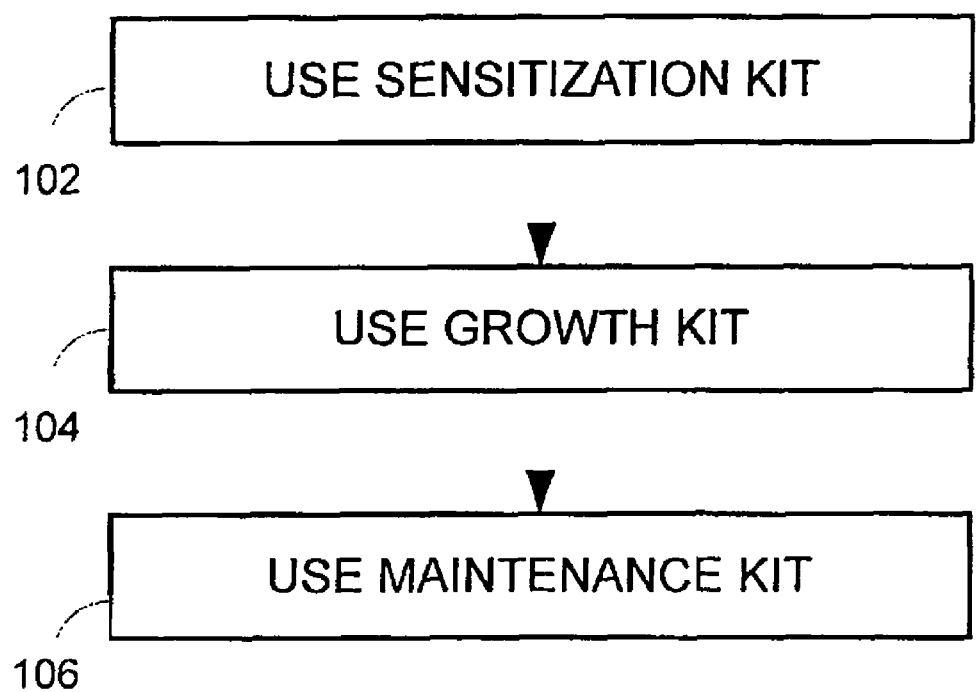
FIG. 1 is a flow chart depicting an illustrative method of treating hair loss in accordance with embodiments of the invention.
Figure 2:
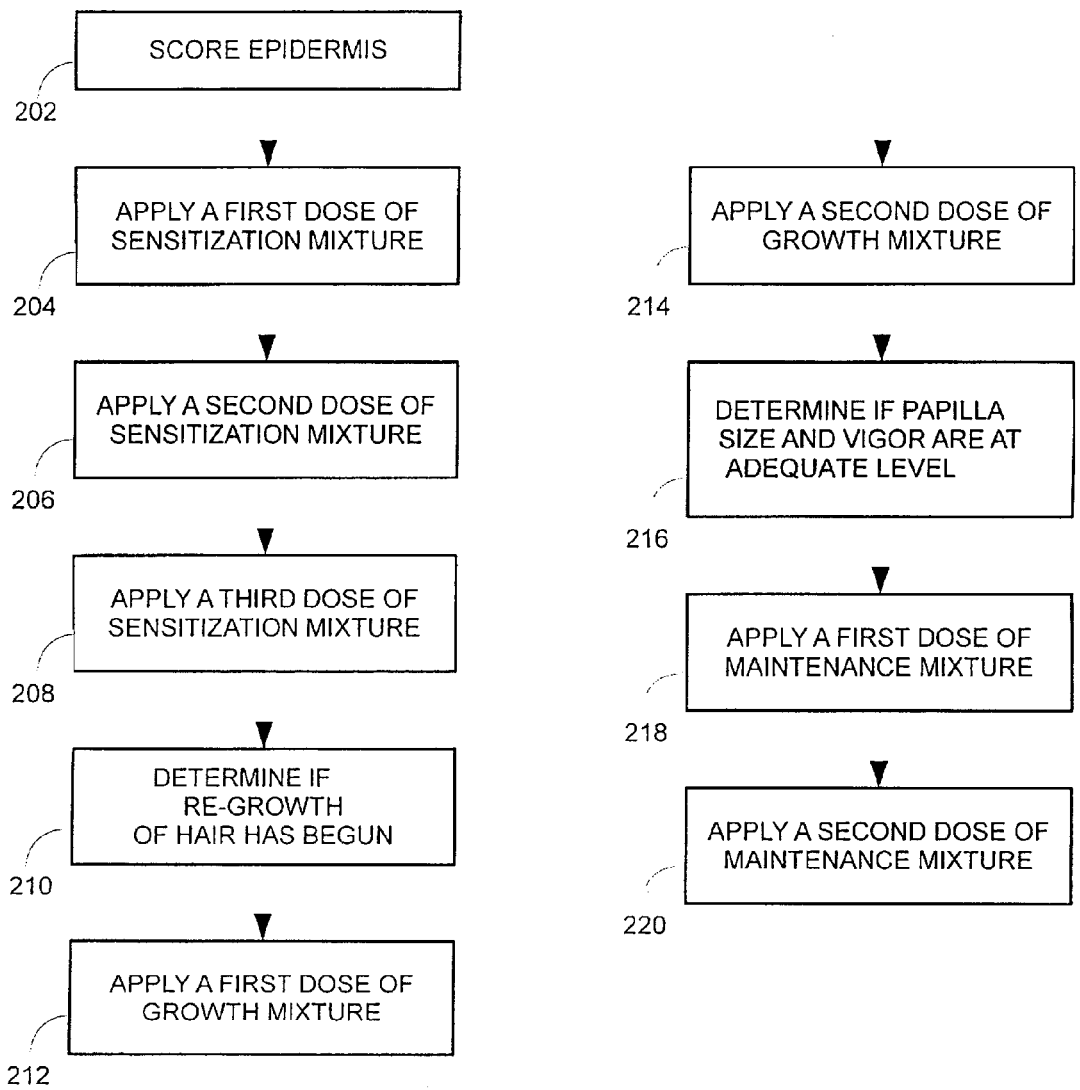
FIG. 2 is another flow chart depicting an illustrative method of treating hair loss in accordance with embodiments of the invention.

With reference to the Drawings, and, in particular, to FIG. 1, a flow chart is presented that depicts an illustrative method of treating hair loss. As the term is used herein, "treating" can include any level of treating (e.g., partially treating, completely treating, maintaining a status quo associated with a condition, etc.), any level of preventing (e.g., partially preventing, completely preventing, preventing a change in a status quo associated with a condition, etc.), or any combination thereof. Additionally, it should be understood that any number of additional steps and any number of variations on the steps described herein can be utilized in various embodiments of the invention.

At a first illustrative step, step 102, a hair-loss patient uses a sensitization kit. The sensitization kit facilitates sensitization of the immune system response, thereby increasing effectiveness of the overall hair loss treatment method. According to various embodiments of the invention, the sensitization kit includes one or more doses at different and graduated concentration levels of a sensitization mixture. The sensitization mixture includes Urushiol. In some embodiments, the sensitization kit includes one dose of the sensitization mixture, while, in other embodiments, the sensitization kit includes a number of doses of the sensitization mixture. In some kits each dose of the sensitization mixture may vary from one or more of the others in the level (increase or decrease) of Urushiol it contains; in others the doses are all uniform but may be applied in combination to determine the appropriate dosage to obtain sensitization.

According to various embodiments of the invention, an illustrative sensitization kit can include a number of graduated doses of the sensitization mixture. As the term is used herein, "graduated doses" refers to doses that increase in size (e.g., volume of the sensitization mixture associated with the dose), strength (e.g., concentration of Urushiol contained within the dose), or a combination of size and strength. In embodiments, for example, each graduated dose of the sensitization mixture can include a different (e.g., increasing) amount of the sensitization mixture. In other embodiments, each dose of the sensitization mixture can include a different (e.g., increasing) amount of Urushiol (in which case, each dose can, but does not necessarily, include the same volume of sensitization mixture, but with different concentrations of Urushiol). In further embodiments, multiple doses in a sensitization kit can include the same amount of sensitization mixture and/or Urushiol. Any number of combinations or variations of the above also are contemplated as being within the ambit of the present invention. The dosages are typically applied in ascending order to determine the sensitization level of the individual. The epidermis may be scored before application if desired.

Embodiments of the sensitization mixture can include extracted Urushiol, engineered Urushiol, or a combination of extracted Urushiol and engineered Urushiol. Extracted Urushiol is Urushiol that is extracted from a natural source. Extracted Urushiol can include Urushiol extracted from any natural source or combination of natural sources. Natural sources of Urushiol include, but are not limited to, plants of the Toxicodendron genus (e.g., poison ivy, poison oak, poison Sumac, etc.), plants in the Anacardiaceae family (e.g., mango, Rengas tree, Burmese lacquer tree, India marking nut tree, cashew nut tree, etc.), and other plants such as, for example, Ginkgo biloba.

Engineered Urushiol is Urushiol that is engineered, rather than extracted from a natural source. In various embodiments, engineered Urushiol can be optimized (i.e., the effectiveness of the engineered Urushiol can be enhanced or selected to lengthen or shorten the period when the skin is in a sensitized state) by the pattern of dosages employed, and the carrier with which the Urushiol is mixed. Engineered Urushiols may be included in the sensitization mixtures According to embodiments of the invention, the sensitization mixtures can include one or more other chemical agents in addition to Urushiol (natural or engineered) such as, for example, dinitrochlorobenzene (DNCB), diphenylcyclopropenone (DPCP), or SADBE. Additionally, in embodiments, the sensitization kit can include other chemical agents to be applied by the hair loss patient such as, for example, corticosteroids, androgenic receptor antagonist agents, caffeine, Ketoconazole, Dihydrotestosterone inhibiting agents, thyroid hormones, prostaglandins or the like. In some embodiments, the sensitization mixture can include any one or more of these additional chemical agents, while, in other embodiments, any one or more of these chemical agents can be applied independently of the sensitization mixture, as part of the sensitization kit.

In various embodiments, the sensitization mixture and/or other chemical agents can be integrated with any number of various application mechanisms such as, for example, alcohol, acetone, aqueous or other solvent delivery systems, wipes (e.g., pre-moistened wipes), cream, lotion, powder, gel, or the like. In an embodiment, for example, the sensitization mixture is applied using a roll-on applicator. In another embodiment, for example, the sensitization mixture is applied using a spill-proof blotter applicator. In embodiments, the applicators and other containers described herein can be equipped with child-resistant lids or other safety devices. Similarly, the chemical agents employed in the various mixtures described herein can include taste bitterants, fragrances, and the like. It should be understood that the sensitization kit and mixture, as well as the re-growth 104 and maintenance kits 106, can include any or all of these additional items and features to facilitate effectiveness, safety, and the like. For example, in some embodiments, the sensitization kit includes sterile sandpaper packets or sticks for scoring the epidermis prior to application of chemical agents. These may continue to be used during growth and maintenance phases.

This engineered Urushiol and SADBE, and or other commonly used contact dermatitis agents mixture, is hereby introduced as a poly-haptenol mixture employed in the sensitization kit. After sensitization occurs, and the sensitization dosage level is determined, a subsequent treatment referred to at FIG. 1 as use of the Growth kit (104) comprising application of a growth-enhancing mixture is employed. Preferably, the growth kit includes a growth mixture comprising at least one and preferably a mixture of thyroid hormones T3, T4, T1a and T0a and other hormones such as prostaglandins and prostaglandin analogs in addition to urushiol at or near the sensitization level determined previously. The growth mixture is applied topically directly to the papilla and follicle increasing papilla vigor and size. This is the growth kit 104. It is designed to rapidly initiate growth after the sensitization phase has rendered the immune system attack on the hair follicles ineffective. The growth-enhancing mixture may include multiple doses to be applied at scheduled intervals. The doses may be the same, graduated, or may be varied, all as related to the level of thyroid hormone or hormones. The doses or some of the doses may include Urushiol and the same or varied levels or at or near the sensitization leve determined previously. The growth kit may direct the user to apply the doses in predetermined order or to change from one dose to another based on one or more physical results. Lastly, a maintenance kit 106 for longer term use to maintain the results produced from the initial treatment is used. FIG. 1 (106). The maintenance kit may contain multiple doses of a maintenance mixture. The maintenance mixture may comprise one or more thyroid hormones, prostaglandins or Urushiol, or two or more hormones. The relative levels of hormones or Urushiol or both may differ from dose to dose or be uniform, and the kit may include a recommended order of doses to accomplish a pattern intended to maintain the hair growth. Alternatively, the kit may include description(s) of one or more physical results.

If the maintenance kit seems to lose its effect for inducing hair regrowth, the method may be re-applied in its entirety, or partially. The growth kit may be employed; or the sensitization kit may be used again, partially or entirely, depending on its effects, to re-determine a sensitization level.

The topical doses of Thyroid and other hormones employed by the kits and the method as a whole are considered non-therapeutic surface doses because they are only delivering a non-therapeutic amount of thyroid hormone systemically to the blood and a therapeutic dose directly to the papilla. Papilla and Follicular response to Thyroid hormone treatment increases the size and vigor of the papilla and follicle in rats and mice.

In order to dramatically increase alopecia treatment success, the first phase of treatment, referred to as sensitization, must be optimized. Although it is possible to simply start with a growth kit that includes a dose that causes sensitivity in many people and this invention includes such an embodiment, the proposed optimization includes providing a graduated dosage sensitization kit including multiple chemicals, some of which may be engineered, to facilitate the sensitization reaction necessary for hair regrowth to start. It is believed that determining the sensitization level for the user may provide a better likelihood of getting results from the least possible exposure. Once regrowth starts, the optional second phase (growth) of treatment can begin. This phase includes continued polyhaptenol sensitization and papilla/follicular growth stimulation by a hormone or a mixture of Triiodothyronine T3, thyroxine T4, iodothyronamine (T1a) and thyronamine (T0a) prostaglandins and prostaglandin analogs. Once hair regrowth starts and papilla size and vigor are increased to sufficient levels, a maintenance kit can be used which contains the same items found in the sensitization and growth kits but provides a schedule and dosages consistent with maintaining hair growth.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

The invention claimed is:

1. An alopecia treatment method, the method comprising:

applying a sensitization kit to determine an appropriate dose of means for inducing contact dermatitis said means comprising Urushiol;

applying a growth kit to induce hair growth, the growth kit comprising a plurality of doses of said means for inducing contact dermatitis, the plurality of doses to be sequentially applied; and applying a maintenance kit to maintain hair growth, the maintenance kit comprising a second plurality of doses of said means for inducing contact dermatitis, the second plurality of doses to be sequentially applied, wherein the frequency of application with the maintenance kit is less than the frequency employed with said growth kit.

2. The method of claim 1, wherein said Urushiol is engineered.

3. The method of claim 1, said sensitization kit containing graduated doses of said means for inducing contact dermatitis, and said means further comprising a variety of synthetically engineered Urushiol haptens for providing different half-lifes.

4. The method of claim 1, the sensitization kit containing a plurality of graduated doses of said means for inducing contact dermatitis comprising Urushiol combined with another material selected from a group consisting of dinitrochlorobenzene (DNCB), diphenylcyclopropenone (DPCP), and SADBE.

5. The method of claim 1, containing a child resistant cap with a roll-on feature.

6. The method of claim 1, wherein each of said kits includes packets of wipes pre-moistened with one from the group consisting of means for inducing contact dermatitis, means for maintaining increased papilla size, and means for maintaining at least one of contact dermatitis, increased papilla size, and increased papilla vigor.

7. The method of claim 1, wherein the growth kit includes a means for increasing papilla size and vigor comprising a mixture of at least two selected from the group consisting of: T3, T4, T1a and T0a.

8. The method of claim 1, wherein the growth kit includes a growth mixture comprising at least one of T3, T4, T1a or T0a, Thyroid hormone, and Hormone metabolites in a cream, lotion, or gel.

* * * * *